United States Patent [19]  
Heinzelmann

[11] Patent Number: 4,611,008  
[45] Date of Patent: Sep. 9, 1986

[54] PREPARATION OF NITROESTERS FOR CORONARY ARTERY THERAPY

[75] Inventor: Walter Heinzelmann, Odenthal, Fed. Rep. of Germany

[73] Assignee: Dynamit Nobel AG, Cologne, Fed. Rep. of Germany

[21] Appl. No.: 650,797

[22] Filed: Sep. 14, 1984

[30] Foreign Application Priority Data

Sep. 17, 1983 [DE] Fed. Rep. of Germany ....... 3333639

[51] Int. Cl.$^4$ ...................... A61K 31/34; A61K 31/21
[52] U.S. Cl. ..................................... 514/470; 514/509
[58] Field of Search ............................... 514/509, 470

[56] References Cited  
U.S. PATENT DOCUMENTS 3,028,307  4/1962  Ninger ................................. 514/509
3,251,739  5/1966  Petersen ............................. 514/509
4,112,115  9/1978  Coghlan .............................. 514/509
4,322,433  3/1982  Leslie et al. ......................... 514/509

OTHER PUBLICATIONS

Chem. Abst. 82:127175j (1975) Tamchyna et al.
Chem. Abst. 99:181480n (1983)–Nitto Electric Ind. Co.
Chem. Abst. 102:12410w (1985)–Enscore et al.
Remington's Pharmaceutical Sci. 1980-pp. 284 & 1264-Mack Publ. Co.

Primary Examiner—Douglas W. Robinson  
Attorney, Agent, or Firm—Felfe & Lynch

[57] ABSTRACT

A gel or gel preparation of improved stability and shelf life having an action on the coronary arteries comprising nitroesters, an oil base and finely disperse silica, wherein the finely disperse silica contains hydrophilic and hydrophobic, finely disperse silica is disclosed. A method for making the gel preparation is also disclosed.

9 Claims, No Drawings

PREPARATION OF NITROESTERS FOR CORONARY ARTERY THERAPY

BACKGROUND OF THE INVENTION

Nitroesters, i.e., nitrates of polyvalent aliphatic or cyclic alcohols are used in the treatment of coronary artery disease, i.e., in the extended treatment of *angina pectoris,* the prevention of attacks, and post-infarction therapy.

Common forms of application are oral and especially transdermal, the latter form permitting a direct and systemic action on the vascular system through the skin acting as a reservoir and controlling membrane, as well as a uniform sustained release of the nitroesters.

Whereas spray preparations are intended mainly for the treatment of acute attacks, unguent preparations, e.g., ointments on the basis of oil-water emulsions and gel preparations, produce a prolonged action due to the nature of the vehicle and also a controlled release of the active nitroester substances.

Especially thixotropic gels formed with skin-penetrating oils on the one hand contain the oil as the vehicle for carrying the active substance through the skin, and on the other hand, by means of the thixotropic agent and any other desired carrier substances, they produce a uniform release of the active substance from the gel to or within the surface of the skin.

The present invention relates to gel preparations of nitroesters having an action on the coronary arteries.

It is known to prepare nitroesters of the kind which will be described in detail below by dissolving them in oils, such as fatty oils, with disperse silica, for example, in the form of gels of a spreadable consistency, whose viscosity is only slightly dependent on temperature.

However, if the gels are let stand for a long time in packaging such as capsules, ointment containers or tubes, a disadvantage is found in the segregation of the liquid oil, which interferes with the use of the gels and impairs the uniform release of the active substances. Also, the separated oil can leak out of the package.

The problem therefore existed of reliably preventing the separation of oils from gel preparations containing the active agents, i.e., of preventing so-called "oiling out."

THE INVENTION

The subject matter of the invention, therefore, is gel preparations and gel-containing preparations of nitroesters, and a method for their production. In accordance with the invention, a hydrophobic silica is used in addition to the common hydrophilic silica as the finely dispersed silica required for the preparation of the gels.

The preparations are preferably thixotropic gels of a transparent to, in some cases, translucent appearance, containing dissolved nitroesters. Transparent gels do not result in all cases when additional solid vehicles for nitroesters are present. In the presence of solid ingredients, such as vehicles and/or ointment bases, preparations result which have gel contents in which the content of hydrophobic silica prevents the separation of the oil base or of liquid nitroesters.

Depending on the quantity ratio of the oil base to the finely disperse silica, the preparations have a variable, continuously controllable viscosity from oily through spreadable to firm.

Accordingly, the preparations are suitable for a variety of application forms, e.g., as salves or skin oils, or as oily to pasty fillings for chewable capsules made, for example, from soft gelatins, as spreadable gel preparations, as gel-like, plastic fillings for adhesive patches, or, lastly, as oily or more or less stiff fillings for capsules for ingestion by swallowing, made, for example, of hard or soft gelatins and the like.

Water is not to be added into the preparations, nor should be present free or bound water in the components of the preparations. Water merely absorbed from the air is tolerated and must not be excluded.

The content of hydrophobic silica suppresses oiling-out, so that no oiling-out occurs during the legal shelf life. It appears, however, that the hydrophobic silica content is also capable not only of providing a substantially improved shelf life, but also of reducing the degradation of the nitroester by the access of moisture.

The anhydrous gel preparations of nitroesters in accordance with the invention, which can be referred to as "oleogels" for the sake of brevity, generally contain proportions of 0.5 to 25.0 weight-parts of the active substance, 55 to 90 weight-parts of an oil base, and 5.0 to 40 weight-parts of finely disperse silica of which 60 to 95% weight-percent consists of hydrophilic silica and 5 to 40 weight-percent, preferably 20 to 40 weight-percent, of hydrophobic silica. Larger or smaller amounts of adjuvant substances may be added, if desired.

In the case of the preferred nitroester solutions, their nitroester content is 0.5 to 25.0, preferably 0.5 to 10 wt.-%, if the nitroester is very soluble, as it is in the case of glycerine trinitrate, but if it is less soluble, as in the case of isosorbide mono-(or di-)nitrate, it is 0.5 to 10 wt.-%. If higher concentrations of the less soluble nitroesters are to be prepared, either they can be suspended in pure form in the oil base, or they can be adsorbed onto solid carriers and suspended in the oil base.

In borderline cases, the contents can also vary from those given. Other materials can be added in small or even in fairly large amounts to the preparations, such as, for example, inert carrier substances for liquid or solid nitroesters.

Preparations made with solutions of the nitroesters contain the latter in amounts of 0.5 to 5.0% of the weight of the preparation. The ratio of hydrophilic silica to hydrophobic silica is to be preferably from 80-60:20-40 percent by weight.

Finely disperse hydrophilic silica is commonly obtained from silicon tetrachloride by flame pyrolysis. The hydrophilic silica does not consist exclusively of the oxide, but also contains some silanol groups at least on the surface. The spherical primary particles of the silica obtained by pyrolysis generally range from 5 to 30 nm and some of them form secondary agglomerates which build up the thixotropic gel structure.

The hydrophobic, finely disperse silica is prepared from the hydrophilic finely disperse silica by treatment with a hydrophobizing agent; a variety of such agents are usable, but alkyl chlorosilanes are preferred. Of the alkyl chlorosilanes the dichlorodialkylsilanes having contents especially of methyl groups or, if desired, ethyl groups are preferred, although monochlorotrialkylsilanes and trichloromonoalkylsilanes having preferably methyl groups or, if desired, ethyl groups, are usable. Preferably the product Aerosil R 972$^R$ of DEGUSSA AG, Frankfurt/West Germany is used as hydrophobic disperse silica.

Common, pharmaceutically acceptable oils are used as the oil base, if they have no turbidity between $-10°$ C. and +30° C., or at least between 0° and 30° C., do not turn rancid, and are virtually immune to bacterial attack in the water-free state. Therefore, if fatty acid moieties are contained in these oils, they are to be saturated fatty acid moieties.

Consequently, the oil base can consist of fluid media having the above-named properties, such as for example saturated triglycerides or partial glycerides, liquid diols such as 1,2-propanediol, liquid polyols, paraffin oils, liquid esterification products of bivalent, trivalent and tetravalent alcohols with saturated straight-chain or branched fatty acids, plus, if desired, additional contents of dicarboxylic acids, as well as liquid esters of the low fatty alcohols with low or medium-chain fatty acids, other corresponding substances, and mixtures thereof.

Preferably, the oil base consists of liquid triglycerides of mixtures of saturated, straight-chain fatty acids of 8 to 12-carbon chain length, which can be mixed, if desired, with liquid paraffin oil. Also suitable are 1,2- and/or 1,3-propanediol or propanediol-fatty acid esters of fatty acids of an 8 to 12-carbon chain length, as well as reaction products of partial glycerides of saturated fatty acids of a 6 to 12-carbon chain length with saturated dicarboxylic acids such as succinic acid, malonic acid or glutaric acid.

Very preferentially, the oil basis consists of triglycerides of saturated fatty acids of an 8 to 12-carbon chain length, or mixtures thereof with liquid paraffin oil, of 1,2-and/or 1,3-propanediol, or of reaction products of partial glycerides, especially diglycerides of the saturated fatty acids of 8 to 12 carbon atoms with succinic acid.

The nitroesters affecting the coronary arteries are especially nitroglycerin, pentaerythritol tetranitrate and the nitroesters of 1,4,3,6-dianhydrosorbide known by the names isosorbide dinitrate and isosorbide-5-mononitrate.

The solid carriers that may be used in some cases as carriers of the nitroesters are, for example, organic carrier substances such as glucose, lactose, sorbitol, mannitol, solid glycerides, crystalline celluloses, starch preparations or the like, as well as inorganic carriers such as Celite, dicalcium phosphate, aluminum oxide, and titanium dioxide, and they may be present in additional amounts of up to 85%, preferably 60%, of the weight of the preparation. It is then to be understood that the quantity ratio of the oil base (b) to silica (c), and the quantity ratio of C-1 to C-2, are to be those of claim 1. The amount of the nitroester, however, can amount to as much as 25% of the weight of the preparation including the solid carrier substance.

It is to be understood that adjuvants, ultraviolet stabilizers, antioxidants, preservatives, skin care agents, perfumes, dyes, wetting agents, and the like can be contained in small amounts in the preparation.

Furthermore, small amounts of esters of additional fatty acids, as well as of additional polyols, univalent alcohols, or their esters, can be contained in the oil base.

The content of hydrophobic finely disperse silica surprisingly not only results in improved shelf life and suppresses the "oiling-out" of the oil base, but also contributes to the stabilization of the preparations and especially prevents the access of water vapor and decidedly reduces the separation of ingredients that is made possible thereby. The viscosity chosen when the preparation was made is accurately maintained for a long period of time. No hydrolysis of the nitroesters or any bacterially caused degradation occurs, even in the case of long storage under, for example, tropical conditions. The addition of bactericides to prevent bacterial breakdown of the preparations has proven unnecessary in virtually water-free preparations.

The production of the gel preparations is generally accomplished by mixing the components in evacuatable stirring vessels at standard pressure or, if desired, at reduced pressure of e.g. 10 to 30 Torr.

The preparation of the invention can be prepared by uniformly mixing the solution of at least one nitroester in the oil base, or the suspension of the nitroester, or the suspension of the nitroester adsorbed onto a carrier substance, and simultaneously or successively a hydrophilic silica and a hydrophobic silica as well as other components, under reduced pressure if desired, and de-airing the mixture until a gel preparation of constant viscosity is obtained.

Preferentially, one sets out from solutions of the liquid or solid nitroesters in the oil base, which in this manner are phlegmatized, and thus are safely handled preparations of the explosive nitroesters.

The suspensions of the nitroester or suspensions of the nitroester adsorbed onto a carrier are also phlegmatized in the preparation and safe to handle in the manufacture of the preparations.

The addition of hydrophilic, finely disperse silica and of hydrophobic, finely disperse silica is performed separately or together, continuously or in one or more portions, by admixing them in amounts which will produce the intended viscosity up to values which remain stable.

To remove gaseous inclusions, the preparations are then stirred under reduced pressure until complete outgassing has been achieved. The viscosities of the preparations depend on the application forms intended. Thixotropic gels or creams are used as gels or salves for topical application, or as filling in injested capsules or in permeable capsules which are fixed by adhesive patches on the skin. Such thixotropic substances are plastic when stirred or dispersed on the skin but are otherwise stiff and do not flow when not moved by an external force. Oils in a liquid state will remain stationary but can be spread in a very thin layer on the skin.

EXAMPLES

Examples 1 to 3 and Comparative Examples A to D

To produce the gel preparations of these examples of the invention and comparative examples, the oil base is placed in an evacuatable ointment mixer and the nitroester is distributed into it by stirring at 20° C. and at up to 35° C. The stated amounts of finely disperse silica, both of the conventional hydrophilic kind and the hydrophobic silica are distributed into the mixture by brief stirring.

To eliminate air, stirring continues for up to 2 hours at reduced pressure (10 to 30 Torr) until the mixture is free of air bubbles.

The preparations are clear transparent gels.

In the test for shelf life, the preparations of the examples of the invention show no separation of the oil base, while in the preparations of the comparative examples some of the oil base separated from the gel.

In the storage, transport and unpacking of the gels in ready-for-sale form, no separation of the oil base is observed in the preparations in accordance with the invention.

In contrast, in the preparations of comparative examples A to D, oily segregations occur, especially upon extended standing and elevated temperature.

EXAMPLES 4 AND 5

The preparations of Examples 4 and 5 of ointment-like consistency are made in a heatable and evacuatable ointment mixer. For this purpose, Miglyol 812 and 829, respectively, are placed in the mixer and the nitroester is dissolved in the Miglyol at room temperature.

The resultant mixture is heated at 45° C. and the rest of the components are dissolved in the oil base by stirring. Then the two types of the finely disperse silica were added successively or simultaneously at 45° C. and the preparation is completed with cooling as in the preceding examples.

The stability in the stability test and in practical handling gives no cause for objection due to "oiling out."

EXAMPLES 6 TO 8

The preparations of Examples 6 to 8 are made by the procedure described in Examples 4 and 5.

The preparation of Example 6, of an unguentous consistency, is made in a heatable and evacuatable ointment mixer. Miglyol-812 or Miglyol-829 is placed in the mixer and heated by means of warm water, with stirring, at 45° C., and first the solid nitroester, isosorbide dinitrate, and then the rest of the components, are dissolved in the oil base by stirring at 45° C. Then the two types of finely disperse silica are added successively or simultaneously at 45° C. and the preparation is completed, with cooling, as in the foregoing examples.

The preparations of Examples 7 and 8 are made as described in Examples 4 and 5, but the nitroester is added at the end together with the solid carrier. For this purpose, in a separate procedure, powdered lactose is placed in a mixer at 20° C. or with cooling, and nitroglycerin is added in portions and uniformly distributed in the lactose, the nitroglycerin being adsorbed onto the lactose (Example 7), Table 2.

A mixture of powdered lactose and isosorbide dinitrate in powder form is prepared in a slowly running mixer in the stated quantity ratios, added in this form to the mixture of the other substances of Example 8, and mixed. The capsule filling of Example 6 and the sustained-action preparations for patches to be adhered to the skin are not transparent, on account of their lactose content, and are of an unguentous consistency.

TABLE 2

| Examples | | 4 | 5 | 6 | 7 | 8 |
|---|---|---|---|---|---|---|
| Oil base | Miglyol 812* | — | 18.6 | 94.9 | 3.0 | 10.0 |
| | Miglyol 829** | 18.4 | — | — | — | — |
| | Softisan 378**** | — | 27.9 | — | — | — |
| | Softisan 701*** | 27.6 | — | — | — | — |
| | Softisan 601**** | — | 46.5 | — | — | — |
| | Softisan 649**** | 46.0 | — | 1.4 | — | — |
| | Paraffin oil | — | — | — | 2.0 | 4.0 |
| Hydrophilic, finely disperse silica | Aerosil 200 | 4.5 | 3.8 | 1.2 | 3.0 | 4.0 |
| Hydrophobic, finely disperse silica | Aerosil R 972 | 1.5 | 1.2 | 0.5 | 2.0 | 2.0 |
| Solid carrier | Lactose | — | — | — | 81.0 | 56.0 |
| Nitroesters | nitroglycerin | 2.0 | 2.0 | — | 9.0 | — |
| | isosorbide dinitrate | — | — | 2.0 | — | 24.0 |
| Product | | Salves | | S | P | P |
| Stability 12 mos. 35° C. (wt. %) | | 0.0 | 0.0 | 0.0 | 0.0 | 0.0 |

***Triglyceride mixture of unsaturated vegetable fatty acids rich in hydroxyl groups
****Triglyceride mixture of saturated vegetable fatty acids
P = sustained-action preparation for plaster patch
S = capsule filling
Examples 4 to 8 are in accordance with the invention.

TABLE 3

| Examples | | 9a | 9b | 10a | 10b |
|---|---|---|---|---|---|
| Oil base | 1,2-propanediol | 85.0 | 30.0 | 85.5 | 41.0 |
| | Miglyol 812* | — | 54.0 | — | — |
| | Miglyol 829** | — | — | — | 45.5 |
| Hydrophilic, finely disperse silica | Aerosil 200 | 8.0 | 8.0 | 8.0 | 8.0 |
| Hydrophilic, finely disperse silica | Aerosil R 972 | 3.0 | 3.0 | 4.0 | 3.0 |
| Nitroesters | nitroglycerin | 4.0 | 5.0 | — | — |
| | isosorbide dinitrate | — | — | 2.5 | 2.5 |
| Product Stability (shelf life) | 6 mos. 35° C. segregation (wt %) | transparent gels no segregation | | | |
| | 12 mos. 35° C. segregation (wt %) | no segregation | | | |

*Neutral oil (triglyceride of the saturated fatty acids, caprylic and caprinic acid).
**Triglyceride of saturated, medium-chain coconut oil fatty acids and succinic acids.
Examples 1 to 10 represent the invention, comparative examples A to D the state of the art.

It will be understood that the specification and examples are illustrative but not limitative of the present invention and that other embodiments within the spirit

TABLE 1

| Example Nos. | | Amounts in wt. % | | | | | | | | |
|---|---|---|---|---|---|---|---|---|---|---|
| | | 1a | 1b | A | B | 2a | C | 2b | 3 | D |
| Oil basis | Miglyol 812* | 87.0 | 67.0 | 87.0 | 67.0 | 85.0 | 85.0 | 60.0 | 85.0 | 85.0 |
| | Miglyol 829** | — | 20.0 | — | 20.0 | — | — | 25.0 | — | — |
| Hydrophilic, finely disperse silica | Aerosil 200 | 8.3 | 8.3 | 11.0 | 11.0 | 9.0 | 12.0 | 9.0 | 8.2 | 11.0 |
| Hydrophobic, finely disperse silica | Aerosil R 972 | 2.2 | 2.7 | — | — | 3.0 | — | 3.0 | 2.8 | — |
| Nitroester | Nitroglycerin | 2.0 | 2.0 | 2.0 | 2.0 | — | — | — | 2.0 | 2.0 |
| | Isosorbide dinitrate | — | — | — | — | 2.5 | 2.5 | 2.5 | 2.0 | 2.0 |
| Product Stability (shelf life) | | Transparent gels | | | | Transparent gels | | | | |
| | 6 mos. 35° C. shrinkage loss | 0.0 | 0.0 | 1.6 | 1.5 | 0.0 | 1.8 | 0.0 | 0.0 | 1.7 |
| | 12 mos. 35° C. shrinkage loss | 0.0 | 0.0 | 2.0 | 2.3 | 0.0 | 2.8 | 0.0 | 0.0 | 2.6 |

*Neutral oil (triglyceride of the saturated fatty acids caprylic and caprinic acid).
**Triglyceride of saturated, medium-chain coconut oil fatty acids and succinic acids.
Examples 1 to 10 represent the invention, Comparative Examples A to D represent the state of the art.

and scope of the invention will suggest themselves to those skilled in the art.

I claim:

1. A gel-containing preparation comprising a coronary-active nitroester selected from the group consisting of nitroglycerin, pentaerythritol tetranitrate and nitroesters of 1,4,3,6-dianhydrosorbide, a pharmaceutically acceptable oil base, and finely disperse silica in the ratio of:
   (a) 0.5 to 25.0 wt.-parts of the nitroester, to
   (b) 55.0 to 90.0 wt.-parts of the oil base, to
   (c) 5.0 to 40.0 wt.-parts of the finely disperse silica, wherein the finely disperse silica consists of 95.0 to 60.0 wt.-% of hydrophilic silica and 5.0 to 40.0 wt.-% of hydrophobic silica.

2. The preparation of claim 1, wherein the finely disperse silica consits of 80 to 60 wt.-% of a hydrophilic silica and 20 to 40 wt.-% of a hydrophobic silica.

3. The preparation of claim 1, containing 1.0 to 10.0 wt.-% of dissolved nitroesters.

4. The preparation of claim 2, containing 1.0 to 10.0 wt.-% of dissolved nitroesters.

5. The preparation of claim 1, containing 2.0 to 5.0 wt.-% of dissolved nitroesters.

6. The preparation of claim 2, containing 2.0 to 5.0 wt.-% of dissolved nitroesters.

7. The preparation of claim 1, further comprising a solid carrier substance for the nitroesters, in amounts of up to 85 wt.-% of the preparation.

8. The preparation of claim 1, wherein the oil base consists of a pharmaceutically acceptable oily liquid substance which is fluid between $-10°$ C. and $+30°$ C.

9. The preparation of claim 7, wherein the oil base consists of a triglyceride of a saturated straight-chain fatty acid of chain length $C_8$ to $C_{10}$.

* * * * *